(12) United States Patent
Olausson

(10) Patent No.: US 8,318,196 B2
(45) Date of Patent: Nov. 27, 2012

(54) FORMULATIONS COMPRISING A VITAMIN AND THE USE THEREOF TO MAKE FORTIFIED FEED AND PERSONAL CARE FORMULATIONS

(75) Inventor: Inger Olausson, Kållekärr (SE)

(73) Assignee: Akzo Nobel N.V., Arnhem (NL)

( * ) Notice: Subject to any disclaimer, the term of this patent is extended or adjusted under 35 U.S.C. 154(b) by 467 days.

(21) Appl. No.: 12/305,714

(22) PCT Filed: Jun. 25, 2007

(86) PCT No.: PCT/EP2007/056293
§ 371 (c)(1),
(2), (4) Date: Jan. 29, 2009

(87) PCT Pub. No.: WO2008/000710
PCT Pub. Date: Jan. 3, 2008

(65) Prior Publication Data
US 2010/0022485 A1    Jan. 28, 2010

Related U.S. Application Data

(60) Provisional application No. 60/816,781, filed on Jun. 27, 2006.

(30) Foreign Application Priority Data

Jun. 27, 2006 (EP) .................................. 06116157

(51) Int. Cl.
*A23K 1/165* (2006.01)
*A61K 31/70* (2006.01)

(52) U.S. Cl. .......................................... 424/442; 514/52
(58) Field of Classification Search ................. 424/442; 514/52
See application file for complete search history.

(56) References Cited

U.S. PATENT DOCUMENTS

| | | | |
|---|---|---|---|
| 3,639,587 A | 2/1972 | Ames | |
| 3,895,117 A | 7/1975 | Backlund | |
| 4,075,333 A | 2/1978 | Josse | |
| 4,572,915 A | 2/1986 | Crooks | |
| 5,484,597 A | 1/1996 | Slavtcheff et al. | |
| 5,962,000 A | 10/1999 | Yanagida et al. | |
| 6,852,332 B2 | 2/2005 | Crepeau et al. | |
| 2006/0008533 A1 | 1/2006 | Habich et al. | |
| 2006/0189662 A1 | 8/2006 | Goto et al. | |

FOREIGN PATENT DOCUMENTS

| | | |
|---|---|---|
| DE | 103 11 585 A1 | 9/2004 |
| DE | 10 2004 061 610 A1 | 6/2006 |
| EP | 0 261 351 A2 | 3/1988 |
| EP | 0 390 930 B1 | 3/1993 |
| EP | 0 571 677 A1 | 12/1993 |
| EP | 0 682 874 B1 | 3/2001 |
| GB | 706607 | 3/1954 |
| GB | 905016 | 9/1962 |
| GB | 1126289 | 9/1968 |
| GB | 1 471 797 | 4/1977 |
| JP | 62-106018 | 5/1987 |
| JP | 5-338095 | 12/1993 |
| JP | 10-101524 | 4/1998 |
| JP | 2005-247786 A | 9/2005 |
| WO | WO 91/02520 | 3/1991 |
| WO | WO 94/15480 | 7/1994 |
| WO | WO 95/03772 | 2/1995 |
| WO | WO 95/28091 | 10/1995 |
| WO | WO 96/11585 | 4/1996 |
| WO | WO 00/25599 | 5/2000 |
| WO | WO 01/70040 A1 | 9/2001 |
| WO | WO 01/70044 A1 | 9/2001 |
| WO | WO 2005/034913 A1 | 4/2005 |
| WO | WO 2005/079143 A2 | 9/2005 |
| WO | WO 2006/024620 A1 | 3/2006 |
| WO | WO 2006/066675 A1 | 6/2006 |

OTHER PUBLICATIONS

International Search Report for International Application No. PCT/EP2007/056293; Completion Date Sep. 13, 2007.
European Search Report for International Application No. 06116157.6-2114; Completion Date Dec. 19, 2006.
Questel English Abstract of Japanese Patent Application No. 5-338095A.
Questel English Abstract of Japanese Patent Application No. 10-101524A.
Questel English Abstract of Japanese Patent Application No. 62-106018A.
English Translation of Japanese Patent Application No. 2005-247786A.

*Primary Examiner* — Renee Claytor
(74) *Attorney, Agent, or Firm* — Norris McLaughlin & Marcus, P.A.

(57) ABSTRACT

The invention relates to aqueous formulations comprising alkoxylated castor oils with 15-25 ethyleneoxy units and a vitamin, preferably a fat-soluble vitamin, as well as to the use of such formulations in the process to administer the vitamin to an animal, or to make personal care formulations comprising the vitamin.

15 Claims, No Drawings

FORMULATIONS COMPRISING A VITAMIN AND THE USE THEREOF TO MAKE FORTIFIED FEED AND PERSONAL CARE FORMULATIONS

This application is a National Phase Application of PCT Application No. PCT/EP2007/056293, filed Jun. 25, 2007, which claims priority to European Patent Application No. 06116157.6, filed Jun. 27, 2006 and U.S. Provisional Patent Application Ser. No. 60/816,781, filed Jun. 27, 2006, respectively.

The present invention relates to aqueous formulations comprising specific ethoxylated castor oils and a vitamin, preferably a fat-soluble vitamin, as well as to the use of such formulations in the process to administer the vitamin to an animal and the use of the vitamin-comprising formulation to make a personal care formulation.

It is known to provide grazing animals such as cattle, sheep, horses, and the like with supplemental vitamins. Such supplements are needed particularly in the case of fat-soluble vitamins, because the animals' requirements of such vitamins are often exceeded by the amount present and available in their daily feed ration. Various forms of fat-soluble vitamin supplements have been used over the years.

Also it is known to add vitamins to personal care formulations such as shampoos, hair conditioners, hair colouring products, body washes, sunscreens, lipsticks, other make-up products, shaving products, lotions, ointments, and creams for topical use. For example various topical creams comprise vitamin E.

U.S. Pat. No. 4,075,333 relates to the use of injectable compositions in which non-ionic surfactants are used together with a solubilizing agent and isopropanol to improve physical and chemical stability. Castor oil ethoxylates are the preferred surfactants. In the examples a castor oil with 35 ethyleneoxy units per molecule is used. Injecting supplements, however, is undesired because of the labour involved and the stress on the animal. Also, the use of solvents and solubilizing aids is undesired.

Similarly, GB 1,126,289 discloses water-free vitamin solutions comprising a non-ionogenic poly(ethylene oxide)-based emulsifier and a solvent. These solutions can be used in producing suspensions that can be combined with suspensions of medicinal substances. In the examples a castor oil ethoxylate with 40 ethyleneoxy units per molecule is used. However, undesired solvents are used and although the solutions are stable, there is no disclosure of a concentrated suspension of vitamin that is stable. Also, there is no disclosure or suggestion to make a fortified feed or drinking water using the solutions or the suspensions made thereof.

WO 00/25599 relates to a process to make fortified feed. The feed is sprayed with a vitamin premix. The premix used is a formulation comprising both water-soluble and fat-soluble vitamins wherein a castor oil ethoxylate with on average 36 EO units per molecule is used as a compatibilizer. It was found that, depending on the actual composition, the formulations suffer from stability problems and the process as disclosed does not allow stable aqueous dispersions to be made of certain single vitamins.

WO 2006/024620 relates to a method of solubilizing a pigment in oil. The formulations comprise 0.1-15% water and it is said that such formulations may also contain vitamins. These formulations are not aqueous vitamin formulations according to the present invention.

When making feed, or a personal care formulation, there is a desire for a flexible process wherein the amount of vitamins added can be controlled for each vitamin, for instance, depending on the vitamin level in the raw materials used. Consequently, one would like to have stable formulations for vitamins, preferably for each single vitamin, that can be mixed with other vitamin formulations and used in any ratio. Similarly, it may be beneficial to administer one or more vitamins to an animal through its drinking water. In that case it depends on the vitamin deficiency in the feed what amounts and types of vitamins are to be added to the drinking water. In this case one would like to have stable formulations for vitamins, preferably for each single vitamin, that can be mixed with other vitamin formulations added to the water in any ratio. Conventional vitamin formulations do not offer such flexibility. Hence there is a continued need for alternatives and improved vitamin formulations for use in the fortification of feed and/or drinking water. Similarly, the use of an aqueous vitamin composition facilitates the preparation of personal care formulations.

After extensive testing it was surprisingly found that stable aqueous formulations comprising more than 10% by weight (% w/w) of water and one or more vitamins of any kind, particularly fat-soluble vitamins, which formulations are suitable for use in the above-identified processes, can be produced economically if a particular compatibilizer is used.

Therefore, the invention relates to aqueous vitamin formulations comprising such a particular compatibilizer, which is a castor oil alkoxylate with on average 15-25 moles of ethyleneoxy (EO) units per mole of castor oil ethoxylate. Preferably, the average amount of EO units per mole of castor oil alkoxylate is 16 or more and in another embodiment it is preferably 24 or less. In other separate embodiments, the invention relates to the use of these formulations for making fortified animal feed and vitamin-containing personal care products, particularly hair-care and skin-care products, such as shampoos, gels, waxes, mousses, lotions, and conditioners for hair and creams, milks, lotions, ointments, toners, mists, sprays, mousses, salves, liniments, rubs, and balms for topical use. The vitamin-containing personal care products include, but are not limited to, water-based sunscreens, moisturizing creams, and shaving gels.

It is noted that WO 95/28091 discloses that a castor oil ethoxylate can be mixed with a pulverulent or granular animal feed to improve the nutritive value of the feed. Further, it is noted that JP-A-10-101 524 discloses that vitamins and non-ionic surfactants, such as castor oil ethoxylates with at least 30 ethoxylene units per molecule, can be formulated with a water-soluble solvent to make emulsions of fat-soluble vitamins for use in skin creams. However, neither of these references discloses or suggests that stable aqueous formulations of a variety of vitamins can be produced with the presently claimed castor oil ethoxylates, nor that such formulations are particularly suited for use in the process of making animal feed.

Further, WO 91/02520 relates to hydrophobic vitamin compositions wherein castor oil ethoxylates are used. However, these oily formulations need to be encapsulated with hard gelatin before use. Such encapsulation is undesired, for it is uneconomical and limits the use of the vitamin formulation. The hydrophobic compositions are not stable aqueous formulations in accordance with the present invention.

The castor oil alkoxylates according to the invention can be produced in any conventional way, as is known to the skilled person. Suitably they are the conventional products obtained by alkoxylation of castor oil from a natural source. However, also technical glycerides of 12-hydroxy-9-octadecenoic acid that have been alkoxylated can be used. Because of their acceptance in foodstuff the alkoxylates preferably are ethoxylates. However, if so desired, they may comprise a certain amount of other alkyleneoxy units, such as propyleneoxy or butyleneoxy units. Preferably, the 15-25 moles of EO units that on average have to be present per molecule are in the form of an EO block. The castor oil or the glycerides of 12-hydroxy-9-octadecenoic acid can be wholly or partially hydrogenated to further control the compatibilizing effect. Preferably, the castor oil alkoxylate is ethoxylated castor oil from a natural source.

As indicated, the use of these castor oil alkoxylates makes it possible to prepare aqueous stable formulations of any vitamin based on the same castor oil alkoxylate. Since the same compatibilizer is used, the aqueous vitamin formulations may be mixed in any ratio without any problem, if so desired, allowing great flexibility in the addition level for each vitamin in the fortification process or in the formulation of personal care products. Preferably, the aqueous formulations of the present invention are not encapsulated.

The aqueous vitamin formulations according to the invention can be added to feed or water in any way desired.

If they are added to feed, the following is to be taken into consideration:

i) if the vitamin formulations are pelletized, the moment of adding them to the feed may be either before or after the pelletization step. Because of the heat involved and the sensitivity of some vitamins to heat, it may be beneficial to add the vitamin formulation to the feed after said pelletization step. If desired, at least one vitamin formulation may be added before the pelletization, while at least one other vitamin formulation is added after the pelletization. Preferably, at least one vitamin formulation is added after pelletizing the feed.

ii) in another embodiment of the invention, a pelletized feed is cooled before the vitamin formulation is added. Preferably, pellets are cooled to a temperature below 50° C., more preferably to a temperature of 25-35° C., before the vitamin formulation is added.

iii) in a further embodiment, the vitamin formulation is sprayed onto the feed or the pellets, using conventional spraying equipment, with the spraying equipment preferably being controlled in order to spray the desired amount of vitamin onto the feed.

If added to water, the one or more vitamin formulations are suitably mixed with the water using any conventional means, such as in-line dosing and mixing equipment, or using a mixing tank which can be off-line or in-line with drinking water supply means.

The aqueous vitamin formulations according to the invention can be used to make vitamin-containing personal care products by simply combining one or more aqueous vitamin formulations with either the personal care product to which the vitamins are to be added, or by combining it/them with one or more raw materials for making the personal care product. If more than one vitamin is to be present in the final product, then the vitamins can be added together or separately to one or more raw material feeds and/or the personal care product itself.

The vitamins formulated according to the invention can be any of all vitamins. Also combinations of vitamins can be formulated in one single formulation. However, for utmost flexibility it is desired to formulate the vitamins separately. The vitamins can be used in any form. Suitable forms include the pro-vitamin, ester, and salt forms. For example, vitamin B can be used in predominantly the riboflavin form or the sodium riboflavin phosphate form. Since stability and compatibility typically are not an issue for vitamins which are completely water-soluble, one embodiment of the present invention relates to the use of the specified castor oil alkoxylates in aqueous vitamin formulations where not all vitamin is dissolved in the aqueous phase. Since the benefits are most pronounced with fat-soluble vitamins, a preferred embodiment according to the invention relates to formulations according to the invention wherein at least one fat-soluble vitamin is present. Typical examples of fat-soluble vitamins include vitamins A, D, particularly D3, E, and K (all in various forms). Also Vitamin F (essential fatty acids) can be formulated very well in a composition according to the invention.

In one embodiment of the invention, the vitamin formulation is an aqueous concentrate. Using a concentrated formulation allows production at one location and use of the concentrate in a formulation process at another location while reducing handling requirements. Before being used in the formulation process, the concentrate may be diluted if so desired. The concentrates suitably contain more than 5% w/w, preferably more than 7.5% w/w, even more preferably more than 10% w/w, and preferably less than 40, more preferably less than 30% w/w of vitamin. Also, such concentrates suitably contain more than 5% w/w, preferably more than 7.5% w/w, even more preferably more than 10% w/w, and preferably less than 50, more preferably less than 30% w/w of castor oil alkoxylate. The remainder of the concentrate is water, optionally comprising further additives. Typically, the amount of water in the concentrated formulation is more than 10% w/w, preferably more than 15% w/w, more preferably more than 20% w/w of the final formulation, up to 90% w/w, all based on the final formulation. Preferably, the water is present in an amount of 2 to 5 times the amount of castor oil alkoxylate. The further additives are used in an amount of 0-20% w/w, said additives including minerals, enzymes, such as phytase or carbohydrate- and/or protein-splicing enzymes, flavourings, antibiotics, probiotics, preservatives, and optionally other common animal feed additives, provided that these additives have no adverse effect on the vitamin, the castor oil alkoxylate, or the stability of the concentrate. It is noted that there is no upper limit to the amount of castor oil alkoxylate used, except that economics will dictate to use as little of it as possible. It is furthermore noted that after further dilution with water, the amount of water can increase to 99.9998% w/w, the amount of vitamin, castor oil alkoxylate, and optional further additives being as low as 0.0001% w/w.

The castor oil alkoxylates according to the invention were observed to be very good compatibilizers, particularly for fat-soluble vitamins, and therefore they can be used in the aqueous formulations in very low amounts. In one embodiment, the formulations according to the invention comprise fat-soluble vitamins. Independently of the types of vitamins in the formulation and the intended use, in another embodiment of the invention the formulation comprises 0.5 to 2 parts by weight of castor oil alkoxylate per part by weight of vitamin. Preferably, an amount of more than 0.75, more preferably more than 0.9 parts by weight, and preferably less than 1.5, more preferably less than 1.4 parts by weight of the castor oil alkoxylate is used per part by weight of vitamin.

It is noted that the term "feed" as used throughout this document is meant to denominate any nutritious substance used for feeding animals and includes, for instance, fats; cereals, such as meal of wheat, oats, barley, maize, and rice, or these cereals in the crushed state; vegetable protein feed based on, e.g., rape, soya, and sunflower; animal protein feed, such as meat meal, blood meal, bone meal, and fish meal; molasses; and milk products, such as various milk powders and whey powders.

The term "fat-soluble" is used for those compounds which have a solubility at 20° C. of less than 1 g/l in distilled water and more than 1 g/l in soya oil.

Animal feed according to the invention usually contains 0-80% w/w, preferably 10-70% w/w of cereals; 0-15% w/w, preferably 0-10% w/w, and most preferably 1-8% w/w of feed fat; 0-70% w/w, preferably 10-50% w/w of protein-containing nutritious substances other than cereals; and 0-12% w/w, preferably 1-10% w/w of minerals, enzymes, such as phytase or carbohydrate- and/or protein-splicing enzymes, flavourings, antibiotics, probiotics, and optionally other common animal feed additives.

Further additives that can be used in making feed include amino-acids, such as lysine, methionine, threonine, leucine, isoleucine, glutamic acid, and tryptophane, solvents, such as C1-3 alcohols, and C2-12 glycols, such as propylene glycol, sequestering agents, such as EDTA, colorants, flavourings, and pH controlling agents, such as acids, lye, or buffering solutions. It is noted that it is preferred not to use solvents, meaning that solvent levels in the feed preferably are below 1% w/w; in a vitamin formulation directly administered to the animal they preferably are below 4% w/w, and in a concentrated vitamin formulation used, for instance, as an intermediate to make the feed or formulation, below 10% w/w.

Personal care formulations according to the invention preferably contain 0.001-20, preferably 0.002-10, more preferably 0.003-5% w/w of vitamin.

Typically, the personal care formulation will comprise one or more of the usual ingredients, such as, but not limited to, further surfactants, enzymes, liposomes, bleaching agents, or a bleach precursor, anti-wrinkle compounds, dye fixative, dye transfer inhibitors, anti-redeposition polymers, anti-foam agents, foaming agents, perfumes, silicone compounds, vegetable oil, plant extracts, anti-oxidants, antimicrobial agents, moisturizers, nutrients, colorants, fillers, pH buffers, and mixtures thereof. The colorant may be a dye or a pigment. For aqueous personal care formulations dyes are typically preferred, since they are water-soluble and thus more easily incorporated into the formulations compared to pigments, which typically are not water-soluble.

EXPERIMENTAL

Chemicals used:
CO20EO=castor oil ethoxylate with 20 EO units per mole ex Akzo Nobel
CO28EO=castor oil ethoxylate with 28 EO units per mole ex Akzo Nobel
CO36EO=castor oil ethoxylate with 36 EO units per mole ex Akzo Nobel
Water is demineralized water

Example 1 and Comparative Examples A-B

Castor oil ethoxylates were evaluated in formulations with various vitamins by mixing 4 g of a vitamin with 4 g of the castor oil ethoxylate and subsequently adding 28 g water. All ingredients were preheated to 50° C. The transmission (light passing the through the emulsion) was measured using standard Turbiscan™ LAb equipment ex Formulaction. In the evaluation of the samples the highest transmission is looked for, since it indicates a clearer (and better) formulation.

The following results were obtained:

| Vitamin | Producer | Example 1 CO20EO | A CO28EO | B CO36EO |
|---|---|---|---|---|
| Vit E oil | Impextraco | 61.6 | 53 | 0.2 |
| Vit E oil | Impextraco | 63.1 | 53.8 | 3 |
| Vit A acetate | Zhejiang NHU | 2.2 | Not stable | 0 |
| Vit $D_3$ | Vitamin masters | 56.7 | 64.4 | 2 |

Only the CO20EO was found to give acceptable results in all of these tests. Also it was found that in order to get a stable formulation, it is not necessary to have a perfectly clear solution.

Example 2

Vitamin E oil (Impextraco) and a 50/50% w/w mixture of vitamins A and D were formulated with CO20EO and sufficient water was added to form an aqueous formulation such that the viscosity was below 500 mPa·s (Brookfield DV-II/Spindle 31/100 rpm).

The following table shows the composition of the resulting formulations. All quantities are in grams.

| Vitamin E | Vitamin A/D | CO20EO | Water |
|---|---|---|---|
| 4 | 0 | 2 | 6 |
| 4 | 0 | 4 | 11 |
| 4 | 0 | 6 | 17 |
| 4 | 0 | 8 | 22 |
| 0 | 4 | 2 | 10 |
| 0 | 4 | 4 | 10 |
| 0 | 4 | 6 | 15 |
| 0 | 4 | 8 | 22 |

The formulations were all stable and could be used "as such" to administer the vitamin to the animal. They can also be used to spray onto feed to fortify it or used in personal care formulations. If so desired, they may be diluted with water to make drinking water with a desired vitamin level. If so desired, two or more of the formulations may be combined before being used.

The invention claimed is:

1. An aqueous vitamin formulation comprising more than 20% by weight of water, based on the final formulation, at least 5% by weight of one or more vitamins and a castor oil alkoxylate with on average 15-25 moles of ethyleneoxy units per mole of castor oil alkoxylate.

2. A formulation according to claim 1 wherein the castor oil alkoxylate is a castor oil ethoxylate.

3. A formulation according to claim 1 wherein at least one vitamin is fat-soluble.

4. A formulation according to claim 1 comprising 0.5 to 1.5 parts by weight of castor oil alkoxylate per part of vitamin.

5. A formulation according to claim 1 comprising up to 50% by weight of vitamin.

6. Process of making animal feed comprising adding an aqueous vitamin formulation comprising more than 20% by weight of water, based on the final formulation, at least 5% by weight of one or more vitamins and a castor oil alkoxylate with on average 15-25 moles of ethyleneoxy units per mole of castor oil alkoxylate to feed.

7. Process according to claim 6 comprising spraying the vitamin formulation onto the feed.

8. Process according to claim 7 further comprising pelletizing the feed before it is sprayed with the vitamin formulation.

9. A vitamin formulation according to claim 1 wherein the vitamin formulation is capable of being administered to an animal.

10. A vitamin formulation according to claim 9 wherein the vitamin formulation is added to the feed of the animal.

11. A vitamin formulation according to claim 9 wherein the vitamin formulation is added to the drinking water of the animal.

12. A personal care formulation comprising the vitamin formulation of claim 1.

13. A formulation according to claim 1 further comprising additives in an amount of from 0 to 20% by weight.

14. A formulation according to claim 1 comprising 0.75 to 1.3 by weight of castor oil alkoxylate per part of vitamin.

15. Process according to claim 8 further comprising cooling the feed before it is sprayed with the vitamin formulation.

* * * * *